(12) United States Patent
Shimizu (10) Patent No.: US 10,211,027 B2
(45) Date of Patent: Feb. 19, 2019

(54) METHOD FOR MEASURING RESOLUTION OF CHARGED PARTICLE BEAM AND CHARGED PARTICLE BEAM DRAWING APPARATUS

(71) Applicant: NuFlare Technology, Inc., Yokohama-shi (JP)

(72) Inventor: Yukitaka Shimizu, Yokohama (JP)

(73) Assignee: NuFlare Technology, Inc., Yokohama-shi (JP)

( * ) Notice: Subject to any disclaimer, the term of this patent is extended or adjusted under 35 U.S.C. 154(b) by 12 days.

(21) Appl. No.: 15/662,495

(22) Filed: Jul. 28, 2017

(65) Prior Publication Data

US 2018/0040456 A1  Feb. 8, 2018

(30) Foreign Application Priority Data

Aug. 3, 2016  (JP) .................................. 2016-152946
Oct. 13, 2016  (JP) .................................. 2016-201835

(51) Int. Cl.

| | |
|---|---|
| G01B 7/00 | (2006.01) |
| H01J 37/305 | (2006.01) |
| G03F 7/20 | (2006.01) |
| H01J 37/04 | (2006.01) |
| H01J 37/22 | (2006.01) |

(Continued)

(52) U.S. Cl.
CPC ............ H01J 37/305 (2013.01); G01N 21/21 (2013.01); G01N 21/9501 (2013.01); G01N 21/956 (2013.01); G03F 7/20 (2013.01); G03F 7/70091 (2013.01); G03F 7/70258 (2013.01);

(Continued)

(58) Field of Classification Search
None
See application file for complete search history.

(56) References Cited

FOREIGN PATENT DOCUMENTS

| | | | |
|---|---|---|---|
| JP | 56068356 A | * | 6/1981 |
| JP | 05083315 A | * | 4/1993 |

(Continued)

OTHER PUBLICATIONS

Makoto Hiramoto et al. "Beam Blur Analysis of Electron Beam Writer," NuFlare Technology, Inc., 30a-ZL-1, 2006, pp. 2 (with English Translation).

*Primary Examiner* — Andrew Smyth
(74) *Attorney, Agent, or Firm* — Oblon, McClelland, Maier & Neustadt, L.L.P.

(57) ABSTRACT

In one embodiment, a method for measuring a resolution of a charged particle beam includes changing a focus position of the charged particle beam in a height direction, and scanning a dot mark formed on a substrate with the charged particle beam for each focus position, detecting a reflected charged particle reflected from the dot mark for each focus position, calculating a scattered charged particle distribution from a detection result of the reflected charged particle for each height corresponding to the focus position, performing a convolution operation on an approximate expression of a beam waveform of the charged particle beam and a mark shape of the dot mark, the approximate expression including an aperture angle and a resolution of the charged particle beam as parameters, and calculating the aperture angle and the resolution by fitting the scattered charged particle distribution by height and a calculation result of the convolution operation.

14 Claims, 5 Drawing Sheets

(51) Int. Cl.
*H01L 21/027* (2006.01)
*G01N 21/21* (2006.01)
*G01N 21/956* (2006.01)
*G01N 21/95* (2006.01)

(52) U.S. Cl.
CPC .............. *H01J 37/04* (2013.01); *H01J 37/22* (2013.01); *H01L 21/027* (2013.01)

(56) References Cited

FOREIGN PATENT DOCUMENTS

| | | | |
|---|---|---|---|
| JP | 05153492 A | * | 6/1993 |
| JP | 2005-147671 | | 6/2005 |
| JP | 2005147671 A | * | 6/2005 |
| JP | 2007-188671 | | 7/2007 |
| JP | 2007188671 A | * | 7/2007 |
| JP | 2007-234263 | | 9/2007 |
| JP | 2007234263 A | * | 9/2007 |
| JP | 2012-169291 | | 9/2012 |
| JP | 2012169291 A | * | 9/2012 |
| JP | 5083315 | | 11/2012 |
| JP | 5153492 | | 2/2013 |
| JP | 5563801 | | 7/2014 |
| JP | 5563801 B2 | * | 7/2014 |
| JP | 5668356 | | 2/2015 |
| WO | WO 2008/152801 A1 | | 12/2008 |

* cited by examiner

METHOD FOR MEASURING RESOLUTION OF CHARGED PARTICLE BEAM AND CHARGED PARTICLE BEAM DRAWING APPARATUS

CROSS REFERENCE TO RELATED APPLICATION

This application is based upon and claims benefit of priority from the Japanese Patent Application No. 2016-152946, filed on Aug. 3, 2016, and the Japanese Patent Application No. 2016-201835, filed on Oct. 13, 2016, the entire contents of which are incorporated herein by reference.

FIELD

The present invention relates to a method for measuring resolution of charged particle beam and a charged particle beam drawing apparatus.

BACKGROUND

The increasing integration of LSIs has led to finer and finer circuit line widths of semiconductor devices. An approach employed to form desired circuit patterns on semiconductor devices uses a step-and-repeat exposure system to reduce and transfer, onto a wafer, a high-precision master pattern (also called a mask, or a reticle particularly when used in a stepper or scanner) formed on a piece of quartz. The high-precision original pattern is written with an electron beam writing apparatus by use of a so-called electron beam lithography technique.

In an electron-beam drawing apparatus, various settings including focusing are performed on the basis of the resolution and the aperture angle of the beam. For example, the beam resolution is calculated on the basis of a predetermined expression from a beam intensity distribution obtained by scanning and applying an electron beam to a dot pattern (metal pattern) on a substrate, measuring reflected electrons, and calculating the beam intensity distribution from the measurement result (for example, see Japanese Unexamined Patent Application Publication No. 2007-188671 and Japanese Unexamined Patent Application Publication No. 2007-234263).

In order to improve the drawing accuracy of the electron-beam lithography systems, it is required to accurately calculate the resolution and the aperture angle of the beam.

DETAILED DESCRIPTION

In one embodiment, a method for measuring a resolution of a charged particle beam includes changing a focus position of the charged particle beam in a height direction, and scanning a dot mark formed on a substrate with the charged particle beam for each focus position, detecting a reflected charged particle reflected from the dot mark for each focus position, calculating a scattered charged particle distribution from a detection result of the reflected charged particle for each height corresponding to the focus position, performing a convolution operation on an approximate expression of a beam waveform of the charged particle beam and a mark shape of the dot mark, the approximate expression including an aperture angle and a resolution of the charged particle beam as parameters, and calculating the aperture angle and the resolution by fitting the scattered charged particle distribution by height and a calculation result of the convolution operation.

An embodiment of the present invention will be described below with reference to the drawings.

Figure 1:
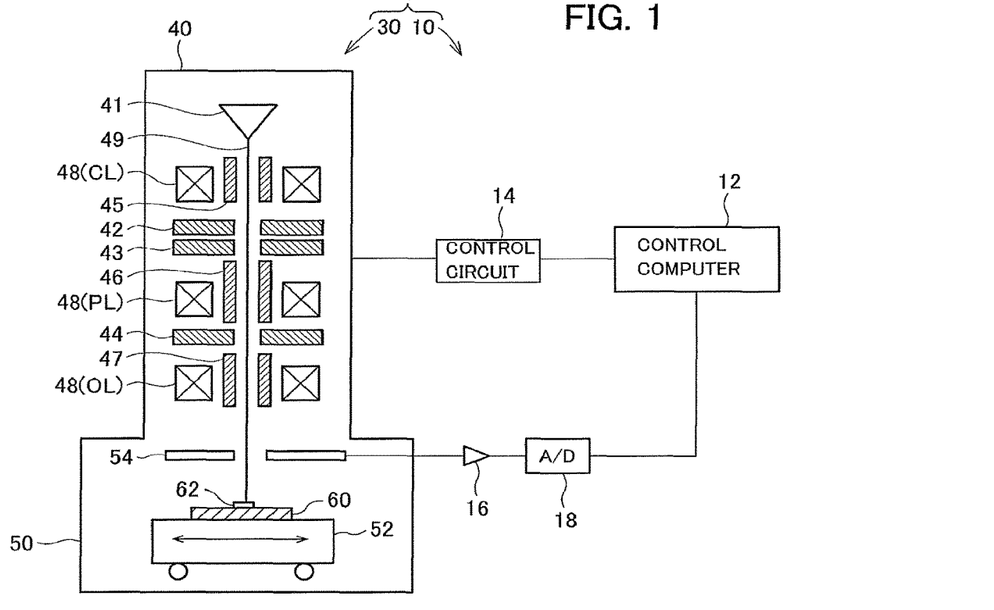
FIG. 1 is a schematic diagram of an electron-beam drawing apparatus according to an embodiment of the present invention.

FIG. 1 is a schematic diagram of an electron-beam drawing apparatus according to an embodiment of the present invention. The drawing apparatus 1 illustrated in FIG. 1 is a variable shaping drawing apparatus including a drawing unit 30 and a control unit 10 that controls the operation of the drawing unit 30.

The drawing unit 30 includes an electron lens barrel 40 and a drawing chamber 50. The electron lens barrel 40 houses an electron gun 41, a blanking aperture 42, a first shaping aperture 43, a second shaping aperture 44, a blanking deflector 45, a shaping deflector 46, an objective deflector 47, and lenses 48 (an illumination lens CL, a projection lens PL, and an objective lens OL).

The drawing chamber 50 houses an X-Y stage 52, which is movably disposed, and a detector 54. A substrate 60 is mounted on the X-Y stage 52. An example of the substrate 60 is a silicon substrate on the surface of which a dot mark 62, which is a metal mark, is formed. The dot mark 62 has a rectangular parallelepiped shape (a quadrangular shape in plan view) and is made of a metal material, such as tungsten or tantalum having higher reflectance than that of silicon. The detector 54 detects reflected electrons reflected from the dot mark 62 by application of an electron beam.

An electron beam 49 emitted from the electron gun 41 provided in the electron lens barrel 40 is controlled by the blanking deflector 45 when passing through the blanking deflector 45 so as to pass through the blanking aperture 42 in a beam-on state and to be deflected in a beam-off state so that the whole of the beam is blocked by the blanking aperture 42. The electron beam 49 that has passed through the blanking aperture 42 during a period from the beam-off state to the beam-on and then to beam-off is one shot of electron beam.

Each shot of electron beam 49 generated by passing through the blanking deflector 45 and the blanking aperture 42 is applied to the first shaping aperture 43 having a rectangular aperture 43a (see FIG. 2) by the illumination lens 48 (CL). The electron beam 49 is shaped into a rectangle by passing through the aperture 43a of the first shaping aperture 43.

Figure 2:
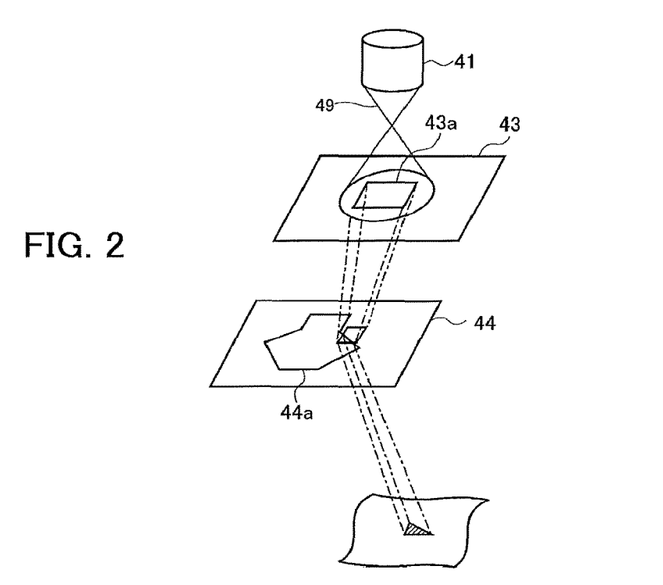
FIG. 2 is a diagram illustrating variable shaping of an electron beam.

The electron beam with a first shaping aperture image that has passed through the first shaping aperture 43 is projected onto the second shaping aperture 44 by the projection lens 48 (PL). The position of the first aperture image on the second shaping aperture 44 is controlled by the shaping deflector 46. This allows the shape and size of the electron beam that passes through an aperture 44a of the second shaping aperture 44 to be varied (variably shaped).

The electron beam that has passed through the second shaping aperture 44 is focused by the objective lens 48 (OL), is deflected by the objective deflector 47, and is applied so as to scan the dot mark 62 on the substrate 60 on the X-Y stage 52.

The control unit 10 includes a control computer 12, a control circuit 14, an amplifier 16, and an A/D converter 18. A signal detected by the detector 54 is amplified by the amplifier 16, is converted to a digital signal by the A/D converter 18, and is transmitted to the control computer 12.

Input and output data of the control computer 12 and data in operation are stored in a memory (not shown) as appropriate. The control computer 12 controls the operations of the components of the lithography system 1. For example, the control computer 12 controls the amounts of deflection performed by the blanking deflector 45, the shaping deflector 46, and the objective deflector 47 via the control circuit 14. The control computer 12 also calculates the resolution and the aperture angle of the electron beam applied in the drawing unit 30.

Figure 3:
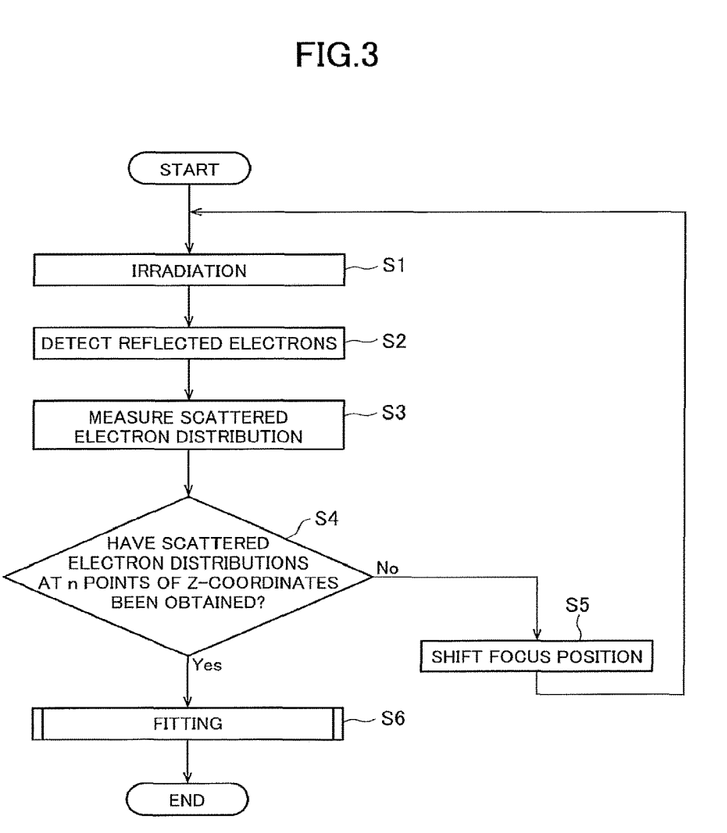
FIG. 3 is a flowchart illustrating a method for measuring a beam resolution and an aperture angle according to the embodiment.

A method for measuring the resolution and the aperture angle of the electron beam will be described using a flowchart illustrated in FIG. 3.

An electron beam is scanned and applied so as to move from the front of the dot mark 62 formed on the substrate 60 onto the dot mark 62 (step S1). The beam size of the electron beam is smaller than the width of the dot mark 62.

Electrons reflected (scattered) from the dot mark 62 by application of the electron beam are detected with the detector 54 (step S2). A signal detected by the detector 54 is transmitted to the control computer 12 via the amplifier 16 and the A/D converter 18.

Figure 4:
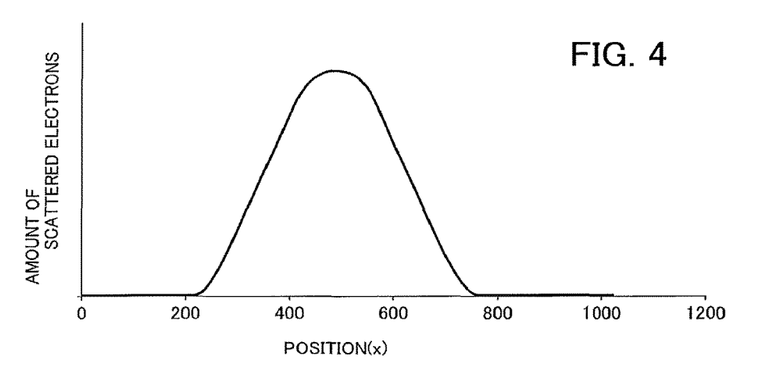
FIG. 4 is a graph showing an example of a scattered electron distribution.

The control computer 12 measures a scattered electron distribution from the result of detection of the reflected electrons (step S3). For example, as the electron beam is scanned, the area of the electron beam overlapping with (applied to) the dot mark 62 increases gradually (first interval), then becomes constant (second interval), and thereafter decreases gradually (third interval). Therefore, with the amount of scattered electrons plotted along the vertical axis, and the beam position along the horizontal axis, the scattered electron distribution has such a waveform that rises at the first interval, becomes constant at the second interval, and falls at the third interval, as shown in FIG. 4. FIG. 4 shows an example of a measurement result scaled to 1,024 points in the horizontal axis direction.

Figure 5:
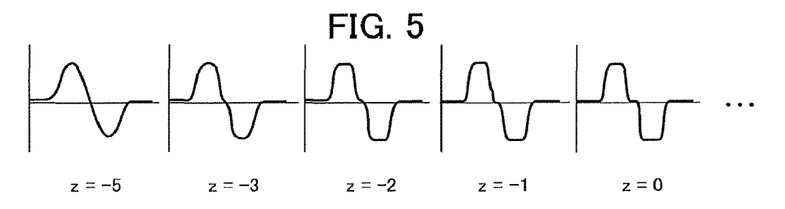
FIG. 5 is a graph showing an example of the differentiated waveform of a scattered electron distribution.

Differentiation of the waveform forms a waveform in which one crest and one trough are consecutive, as illustrated in FIG. 5.

The focus position of the electron beam is shifted in the height direction (the z-direction) to obtain scattered electron distributions at n points (n is an integer equal to or greater than 2) of the z-coordinate (steps S1 to S5). For example, the differentiated waveform illustrated in FIG. 5 is obtained for each z-coordinate.

Note that it is preferable to adjust the electron optical system so that the beam size does not change when the focus position is shifted. Since the intensity of the beam is also included in the fitting target, it is also preferable not to change the sensitivity of the detector 54 every time the focus position is shifted.

Next, a fitting process (step S6) will be described with reference to a flowchart shown in FIG. 6.

The resolution $\sigma(z)$ of the electron beam for each z-coordinate is expressed by the following expression, where $\alpha$ is the aperture angle of the electron beam, and b is a focal shift at the measurement.

$$\sigma(z)=\sqrt{\alpha^2(z-b)^2+\sigma(b)^2} \quad \text{[Exp. 1]}$$

The beam waveform can be expressed by the following approximate expression, where x is the beam position, and h is half of the beam size.

$$\text{erf}\left(\frac{x+h}{\sigma(z)}\right) - \text{erf}\left(\frac{x-h}{\sigma(z)}\right) \quad \text{[Exp. 2]}$$

A beam waveform for each z-coordinate is obtained from the approximate expression using the beam resolution $\sigma$ and the beam aperture angle $\alpha$ (step S61). Assuming that the dot mark 62 is a rectangular parallelepiped, the mark shape is obtained using mark height, mark position, and mark width as fitting parameters (step S62). The beam waveforms obtained at step S61 and the mark shapes obtained at step S62 are each approximated in shape, for example, at 1,024 points on the horizontal axis according to the measurement results at steps S1 to S5.

The control computer 12 performs a convolution operation on each beam waveform obtained at step S61 and the mark waveform obtained at step S62 to calculate a scattered electron distribution for each z-coordinate (step S63). The convolution operation can be executed as follows, for example. First, the frequency components of the beam waveform and the mark shape (for example, the shape is approximated at 1,024 points) are obtained by FFT. Next, the complex conjugates of the frequency component of the beam waveform and the frequency component of the mark shape are multiplied for each frequency component. The results are subjected to inverse FFT.

The measurement results of the n scattered electron distributions obtained at steps SI to S5 are fitted to the calculation results of the convolution operations to find an error (the sum of the squares of the differences in scattered electron intensity at each measurement point on the horizontal axis) (step S65). While the error decreases (step S66: Yes), the fitting parameters are updated (changed) (step S67), and steps S61 to S65 are repeated. $\alpha$ and $\sigma(b)$ when the error does not decrease (the error is minimized) are obtained. This allows the aperture angle and the resolution of the electron beam can be calculate at the same time.

Thus, according to the present embodiment, the scattered electron distribution for each z-coordinate in which the focus position is shifted in the z-direction is measured, and the beam aperture angle $\alpha$ and the resolution a are fitted to the measurement result for each z-coordinate at once. This allows the aperture angle $\alpha$ and the resolution $\sigma$ to be obtained with high accuracy.

The control computer 12 controls the lithography unit 30 so that b at which the resolution becomes the minimum becomes a focus position.

In the above embodiment, the mark shape of the dot mark 62 is assumed to be a rectangular parallelepiped. However, the mark shape is not necessarily the rectangular parallelepiped because of the processing accuracy of the dot mark 62, degradation due to application of an electron beam to the dot mark 62, and so on. For that reason, it is preferable to take into account parameters related to the mark shape as a fitting parameter.

Figure 7:
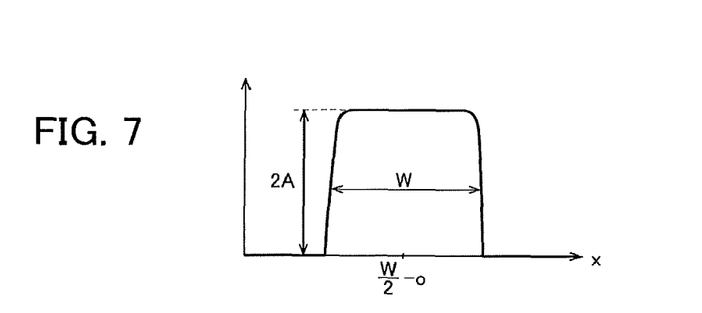
FIG. 7 is a diagram illustrating an approximate example of a mark shape.

For example, the mark shape can be approximated by the following Exp. 3, where A is half of the mark height, o is the mark position, w is the mark width, and δ1 and δ2 are the degradation degree of the mark (for example, the radii of curvature of both edges of the upper surface of the dot mark in the beam scanning direction), as illustrated in FIG. 7. A range in which the value of Exp. 3 is negative is taken as zero.

$$A\left\{2 - \exp\left(-\frac{x+o}{\delta_1}\right) - \exp\left(-\frac{w-(x+o)}{\delta_2}\right)\right\} \quad [\text{Exp. 3}]$$

The control computer 12 performs a convolution operation on the beam waveform of Exp. 2 and the mark shape of Exp. 3 and fitting the measurement results of n scattered electron distributions to the calculation result. The fitting parameters are nine in total, σ(b), α, h, and b for the beam waveform and A, o, w, δ1, and δ2 for the mark shape.

For example, the Gauss-Newton method can be used as a least squares method. In this case the square error is not necessarily be reduced every time a recurrence formula is executed, including an influence of a computational error. For that reason, when the fitting parameters are updated using the recurrence formula, it is preferable that the parameters between the fitting parameters before updating and the fitting parameters after updating be equally divided, (for example, by 100), and points at which the square error is minimized be used as the next fitting parameters. The calculation of the square error and the update of the fitting parameters are repeated to obtain α and σ(b) at which the error is minimized. This allows the aperture angle and the resolution of the electron beam to be calculated at the same time. Since the dot mark shape is also taken into account as a fitting parameter, the aperture angle α and the resolution σ can be acquired with higher accuracy.

Not the Gauss-Newton method but a steepest descent method (fastest descent method) may be used to change the each parameter in proportion to the amount by which the square error decreases when the parameter is slightly changed. Alternatively, the fitting parameters may be obtained so that the error is minimized using another least square method.

Figure 6:
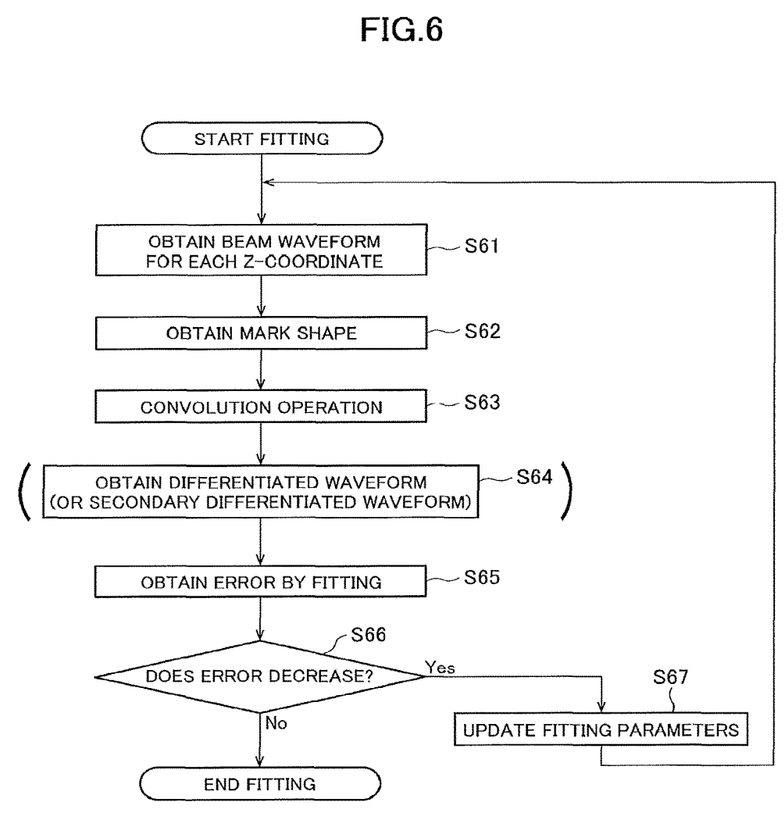
FIG. 6 is a flowchart illustrating a process of fitting the measurement result of the scattered electron distribution and the calculation result.

The fitting target may be the scattered waveform itself, or alternatively, the differentiated waveform or the secondary differentiated waveform of the scattered waveform (step S64 in FIG. 6). When the differentiated waveform is used, the fitting parameters are obtained so that the square error (the sum of the squares of the difference between a derivation of a scattered electron intensity at each measurement point in the horizontal axis direction and a derivation of the result of the convolution operation) is minimized. This also applies to the use of the secondary differentiated waveform.

Figure 8:
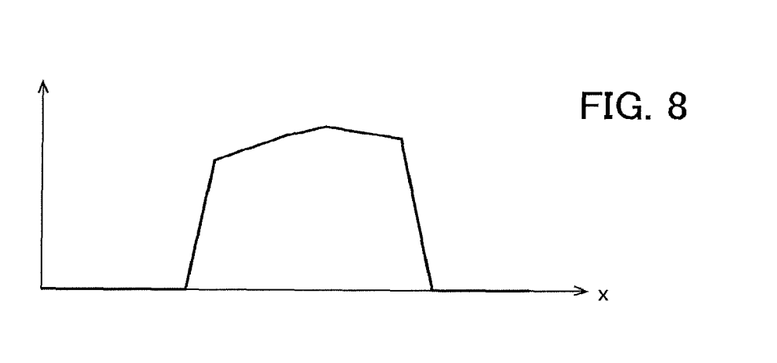
FIG. 8 is a diagram illustrating an approximate example of a mark shape.

The mark shape may not be assumed to be a rectangular parallelepiped. For example, it may be assumed to be an uneven shape with a rectangular cross-sectional shape, or any shape other than a rectangle in cross section, as shown in FIG. 8.

In the above embodiment, the electron optical system is adjusted in measuring the scattered electron distributions so that the beam size does not change when the focus position is shifted. However, it is difficult to adjust it so that a change in beam size is zero. For that reason, it is preferable to also take into account a change in beam size as a fitting parameter.

Furthermore, in the above embodiment, the scattered electron distributions are measured using one dot mark 62 formed on the substrate 60. The fitting accuracy can be improved by measuring the scattered electron distributions using a plurality of dot marks 62.

Figure 9:
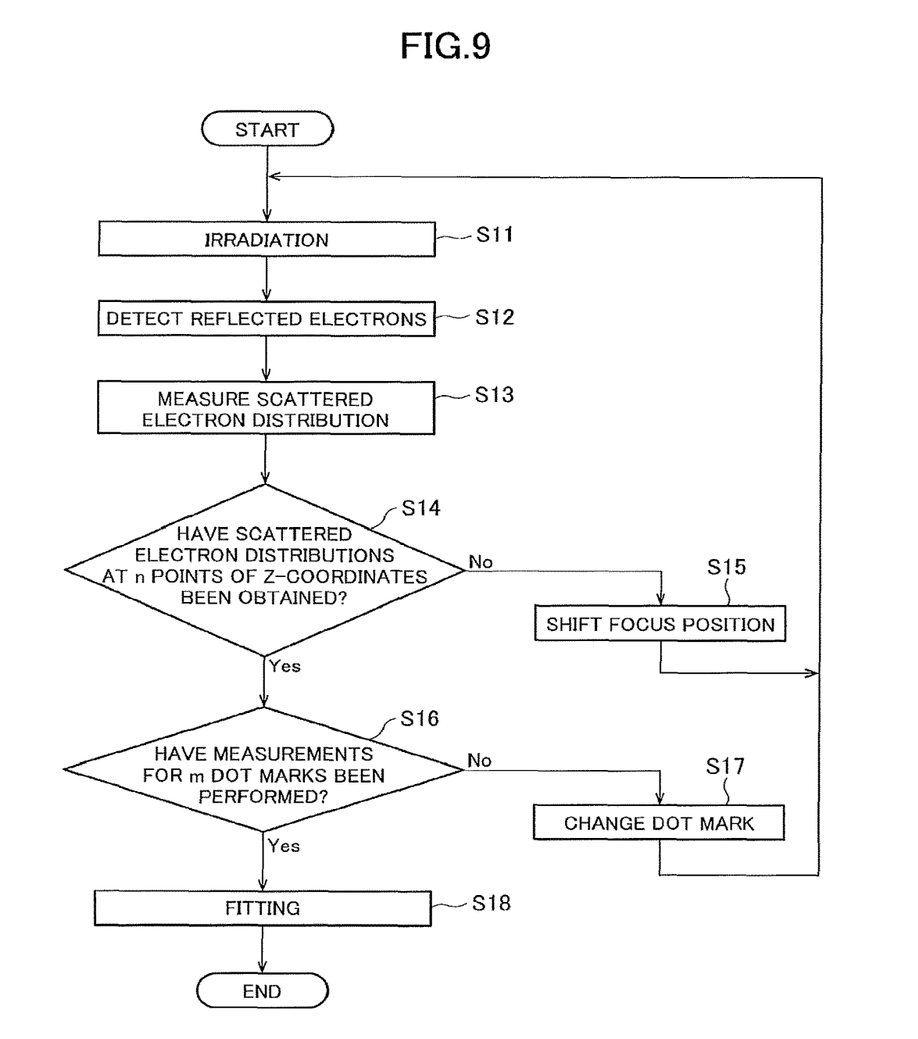
FIG. 9 is a flowchart illustrating a method for measuring a beam resolution and an aperture angle according to another embodiment.

A method for measuring the resolution and the aperture angle of an electron beam by measuring scattered electron distributions using a plurality of dot marks 62 and fitting a change in beam size in this manner will be described with reference to a flowchart illustrated in FIG. 9.

An electron beam is scanned and applied to one of m dot marks 62 (m is an integer equal to or greater than 2) formed on the substrate 60, reflected electrons are detected, and a scattered electron distribution is obtained (steps S11 to S13). Subsequently, the focus position of the electron beam is shifted in the height direction (the z-direction) to obtain scattered electron distributions at n points (n is an integer equal to or greater than 2) of the z-coordinate (steps S14 and S15). The process of steps S11 to S15 is the same as the process of steps S1 to S5 in FIG. 3. The acquisition of the scattered electron distributions at n points of the z-coordinate is performed for m dot marks 62 in sequence (steps S16 and S17).

Although a size change of the beam will also be taken into account as a fitting parameter, as will be described later, the electron optical system is adjusted so that the beam size does not change when the focus position is shifted at the measurement of the scattered electron distributions. The sensitivity of the detector 54 is not changed.

The fitting process (step S18) is the same as the process illustrated in FIG. 6. However, since the change in beam size is also used as a fitting parameter, h in Exp. 2 is set to h(z)=k(z)*h(0). The beam intensity is inversely proportional to the square of the beam size, that is, the beam intensity at the coordinate z is $1/(k(z))^2$ times as high as the beam intensity at z=0.

The number of focal shifts b at measurement in Exp. 1 is made equal to the number of dot marks 62 (m), and the approximate expression of the mark shape in Exp. 3 is prepared by the number (m) of dot marks 62.

To improve the accuracy of phase shift (b) at the measurement, the interval of shifting the focus position in the vicinity of z=0 may be made smaller than that in the other area.

Convolution operations on beam waveforms using m phase shifts b and a plurality of beam sizes h(z) with reference to z=0 in Exp. 1 and approximate expressions of m mark shapes are performed to calculate a scattered electron distribution for each z-coordinate. The measurement results of the scattered electron distributions obtained at steps S11 to S17 are fitted to the operation results of the convolution operations to obtain an error. The fitting parameters are updated, and an aperture angle α and a resolution σ(b) at which the error is minimized are obtained.

Since a change in beam size is also used as a fitting parameter, accurate fitting can be performed even if the fitting target is not the differentiated waveform of a scattered electron distribution but the scattered electron distribution itself. Furthermore, even a scattered electron distribution at a portion where z is great can be subjected to fitting with high accuracy.

Furthermore, the mark degradation degrees $\delta 1$ and $\delta 2$ are used as fitting parameters, the dot mark 62, even if degraded, on the substrate 60 can be used for measuring the scattered electron distributions.

Although the above embodiment has been described as applied to an example in which an electron beam having a beam size smaller than the width of the dot mark 62 is applied to the dot mark 62, there is no limitation on the beam size, because the scattered electron distributions are calculated from the shapes of the dot mark and the beam, and an electron beam having a beam size larger than the width of the dot mark 62 may be applied.

At least part of the control computer 12 described in the above embodiments may be implemented in either hardware or software. When implemented in software, a program that realizes at least part of functions may be stored on a recording medium such as CD-ROM and read and executed by a computer including electrical circuits.

In the above embodiment, a configuration that uses an electron beam as an example of a charged-particle beam is described. Note that a charged particle beam is not limited to an electron beam and may be another charged particle beam, such as an ion beam. While the above embodiment has been described in connection with a single-beam drawing apparatus, the present invention may be applied to a multi-beam drawing apparatus as well.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A method for measuring a resolution of a charged particle beam, the method comprising:
    changing a focus position of the charged particle beam in a height direction, and scanning a dot mark formed on a substrate with the charged particle beam for each focus position;
    detecting a reflected charged particle reflected from the dot mark for each focus position;
    calculating a scattered charged particle distribution from a detection result of the reflected charged particle for each height corresponding to the focus position;
    performing a convolution operation on an approximate expression of a beam waveform of the charged particle beam and a mark shape of the dot mark, the approximate expression including an aperture angle and a resolution of the charged particle beam as parameters; and
    calculating the aperture angle and the resolution by fitting the scattered charged particle distribution by height and a calculation result of the convolution operation.

2. The method according to claim 1, wherein the mark shape is expressed by an approximate expression including height, width, degradation degree, and position as parameters.

3. The method according to claim 2, wherein the degradation degree is a curvature radius of an edge of the dot mark.

4. The method according to claim 1, wherein an electron optical system is adjusted such that the charged particle beam does not change in size when the focus position of the beam is changed in the height direction.

5. The method according to claim 4, wherein a sensitivity of a detector that detects the reflected charged particle is not changed when the focus position of the charged particle beam is changed in the height direction.

6. The method according to claim 1, wherein a plurality of dot marks are formed on the substrate, wherein each dot mark is scanned with the charged particle beam for each focus position, and wherein the scattered charged particle distribution is calculated from a result of detection of the reflected charged particle.

7. The method according to claim 1, wherein the approximate expression of the beam waveform of the charged particle beam includes a change in a size of the charged particle beam in the height direction as a parameter.

8. The method according to claim 1, wherein the aperture angle and the resolution are calculated by fitting a derivation of the scattered charged particle distribution and a derivation of an operation result of the convolution operation.

9. A charged particle beam drawing apparatus comprising:
    a drawing unit including an electron gun, an aperture, an electron lens and a deflector, that changes a focus position of a charged particle beam in a height direction, and scans a dot mark formed on a substrate with a charged particle beam for each focus position; and
    a control computer that calculates an aperture angle and a resolution of the charged particle beam by calculating a scattered charged particle distribution from a detection result of a charged particle reflected from the dot mark for each height corresponding to the focus position, by performing a convolution operation on an approximate expression of a beam waveform of the charged particle beam and a mark shape of the dot mark, the approximate expression including the aperture angle and the resolution as parameters, and by fitting the scattered charged particle distribution by height and a calculation result of the convolution operation.

10. The apparatus according to claim 9, wherein the mark shape is expressed by an approximate expression including height, width, degradation degree, and position as parameters.

11. The apparatus according to claim 10, wherein the degradation degree is a curvature radius of an edge of the dot mark.

12. The apparatus according to claim 9, wherein a plurality of dot marks are formed on the substrate, and wherein the drawing unit scans each dot mark with the charged particle beam for each focus position.

13. The apparatus according to claim 9, wherein the approximate expression of the beam waveform of the charged particle beam includes a change in a size of the charged particle beam in the height direction as a parameter.

14. The apparatus according to claim 9, wherein control computer calculates the aperture angle and the resolution by fitting a derivation of the scattered charged particle distribution and a derivation of an operation result of the convolution operation.

* * * * *